(12) United States Patent
Bosmans et al.

(10) Patent No.: US 10,550,380 B2
(45) Date of Patent: Feb. 4, 2020

(54) METHODS FOR SELECTIVELY ACTIVATING A THERMOSTABLE HYDROLASE

(71) Applicant: PURATOS NV, Groot-Bijgaarden (BE)

(72) Inventors: Geertrui Bosmans, Aarschot (BE); Ellen Fierens, Herent (BE); Kristof Brijs, Zwijndrecht (BE); Jan Delcour, Heverlee (BE); Fabienne Verte, Destelbergen (BE); Jacques Georis, Couthuin (BE); Valérie Dorgeo, Bertrix (BE); Filip Arnaut, Roosdaal (BE)

(73) Assignee: PURATOS NV, Groot-Bijgaarden (BE)

( * ) Notice: Subject to any disclaimer, the term of this patent is extended or adjusted under 35 U.S.C. 154(b) by 0 days.

(21) Appl. No.: 15/525,994

(22) PCT Filed: Nov. 26, 2015

(86) PCT No.: PCT/EP2015/077816
§ 371 (c)(1),
(2) Date: May 11, 2017

(87) PCT Pub. No.: WO2016/083527
PCT Pub. Date: Jun. 2, 2016

(65) Prior Publication Data
US 2017/0321201 A1    Nov. 9, 2017

(30) Foreign Application Priority Data
Nov. 28, 2014  (BE) .................. 2014/5092

(51) Int. Cl.
| | | |
|---|---|---|
| *C12N 9/52* | (2006.01) | |
| *C11D 3/382* | (2006.01) | |
| *A21D 2/08* | (2006.01) | |
| *C11D 3/386* | (2006.01) | |
| *A23K 20/189* | (2016.01) | |

(52) U.S. Cl.
CPC ............... *C12N 9/52* (2013.01); *A21D 2/08* (2013.01); *A23K 20/189* (2016.05); *C11D 3/382* (2013.01); *C11D 3/386* (2013.01); *C12Y 304/21111* (2013.01)

(58) Field of Classification Search
None
See application file for complete search history.

(56) References Cited

U.S. PATENT DOCUMENTS

| | | | |
|---|---|---|---|
| 2005/0255204 A1 | 11/2005 | Arnaut et al. | |
| 2006/0269538 A1* | 11/2006 | Koltermann | ............ C12N 9/64 424/94.63 |

FOREIGN PATENT DOCUMENTS

| | | |
|---|---|---|
| WO | 03/084334 A2 | 10/2003 |
| WO | 2004111220 A1 | 12/2004 |

OTHER PUBLICATIONS

Oledzka et al. Protein Expr Purif. Jun. 2003;29(2):223-9.*
Matsuzawa et al. Eur J Biochem. Feb. 1, 1988;171(3):441-7.*
Zhang et al. Mycopathologia. Mar. 2009;167(3):163-71.*
PCT International Search Report and Written Opinion dated Apr. 15, 2016 for PCT International Patent Application No. PCT/EP2015/077816, 10 pages.
Balti R et al: "A heat-stable trypsin from the hepatopancreas of the cuttlefish (Sepia officinalis): Purification and characterisation," Mar. 1, 2009, Food Chemistry, 113 (2009) 146-154.
Gupta V K et al: "Purification and biochemical characterization of ovine α-1-proteinase inhibitor: Mechanistic adaptations and role of Phe350 and Met356," Feb. 1, 2008, Protein Expression and Purification, 57 (2008) 290-302.
Taylor J C et al: "Familial Temperature Sensitive Alpha 1 Protease Inhibitor (M1ANAHEIM)," Clinica Chimica Acta, 104, 1980, 301-308.
Notification of Transmittal of the International Preliminary Report on Patentability dated May 3, 2017 for PCT International Patent Application No. PCT/EP2015/077816, 8 pages.
Communication Pursuant to Article 94(3) EPC dated Jun. 6, 2018 in connection with European Patent Application No. 15808550.6.
Verbauwhede A E et al., entitled "Thermo-reversible inhibition makes aqualysin 1 from Thermus aquaticus a potent tool for studying the contribution of the wheat gluten network to the crumb texture of fresh bread," Food Chemistry, 264, 2018, 118-125.
ATCC Product Sheet, Soybean Trypsin Inhibitor (ATCC® 30-2104™), 2 pages.
Wellington, JE et al. Dissociation and electrophoretic separation of dextranase and dextranase inhibitor from a tightly bound enzyme-inhibitor complex of Streptococcus sobrinus. Electrophoresis 14: 613-618, 1993.

* cited by examiner

*Primary Examiner* — Christian L Fronda
(74) *Attorney, Agent, or Firm* — Amster, Rothstein & Ebenstein LLP

(57) ABSTRACT

The present invention concerns a method for selectively activating a thermostable hydrolase at a temperature above T1. The present invention provides compositions comprising a thermostable hydrolase and a temperature sensitive inhibitor, wherein said thermostable hydrolase and said temperature sensitive inhibitor form a hydrolase-inhibitor complex at a temperature below T1, but which dissociates at a temperature of about T1. The present invention also relates to uses of said compositions, and a method for preparing said compositions.

7 Claims, 2 Drawing Sheets

METHODS FOR SELECTIVELY ACTIVATING A THERMOSTABLE HYDROLASE

CROSS-REFERENCE TO RELATED APPLICATIONS

This application is a U.S. national stage entry under 35 U.S.C. § 371 of PCT International Patent Application No. PCT/EP2015/077816, filed Nov. 26, 2015, which claims priority to Belgian Patent Application No. 2014/5092, filed Nov. 28, 2014, the contents of which are incorporated herein by reference in their entirety.

FIELD OF THE INVENTION

The present invention relates to a method for selectively activating a thermostable hydrolase at a temperature above T1. The present invention provides compositions comprising a thermostable hydrolase and a temperature sensitive inhibitor, wherein said thermostable hydrolase and said temperature sensitive inhibitor form a hydrolase-inhibitor complex at a temperature below T1, but which dissociates at a temperature of about T1. The present invention also relates to uses of said compositions, and a method for preparing said compositions.

BACKGROUND OF THE INVENTION

The use of thermostable and preferably thermophilic enzymes is highly desired in industry as many enzymatic industrial reactions are performed at high temperatures. Examples include, but are not limited to, the use of peptidases in sectors including, but not limited to, food production and processing such as e.g. cereal processing and baking (e.g. production of bread, pastry), the feed industry (e.g. pet food production), the detergent industry (e.g. laundry detergents), the textile industry (e.g. biopolishing of wool and silk, silk degumming), etc. However, some enzymes induce allergenicity and/or other health issues at ambient temperatures. The application of these enzymes has to be performed with great care. It would therefore be desirable in these and other applications to inactivate the enzyme at lower temperature without compromising the enzyme activity at elevated temperatures. Also, in certain circumstances, for example in food processing, it is undesirable to have enzymes acting at low temperatures, e.g. at room temperature, when other processing steps occur. During these first processing steps enzyme activity is not desired, while in later processing steps at elevated temperature the enzyme activity may be beneficial for the end product quality.

In general, bringing enzyme-inhibitor complexes at higher temperatures simultaneously denatures both, the inhibitor and the enzyme, which does not result in regaining enzymatic activity. Upon heat treatment of the complex between carrot pectin methyl esterase (PME) and its inhibitor (PMEI) from kiwi, enzyme and inhibitor were not driven apart. Yet, the complex denatured (and aggregated) as one entity, following first-order kinetics. Upon pressure treatment, above 300 MPa, the difference in reaction rate of carrot PME with and without PMEI gradually diminished, pointing to a declining amount of inhibited PME. This tendency indicates a pressure-induced dissociation of the PME-PMEI complex. While the liberated kiwi PMEI may be partly inactivated irreversibly, the liberated carrot PME behaves similarly to the other PME present, i.e., a putative reversible inactivation occurs (Jolie et al. (2009) Innovative Food Science & Emerging Technologies 10(4): 601-609). These findings were supported by size exclusion chromatography studies in which the behaviour of the PME-PMEI complex at elevated temperature or pressure levels was determined. Heat treatment proved not to dissociate the complex, but rather to denature the complex as one entity. In contrast, high pressure treatment induced disunion of enzyme and inhibitor, followed by gradual inactivation of PME and PMEI (Jolie et al. (2009) Journal of Agricultural and Food Chemistry 57(23): 11218-11225).

It is an object of the present invention to provide enzyme preparations which are inactive at lower temperatures, but active at elevated temperatures. The use of such enzyme preparations can advantageously reduce or abolish potential health issues associated with the (industrial) application of the enzymes at ambient temperature. Also, in certain applications, the use of enzyme preparations which are inactive at lower temperatures, but active at elevated temperatures, has a beneficial effect on the overall process quality and/or on the quality of the end product (storage, texture, etc.).

SUMMARY OF THE INVENTION

The present inventors have surprisingly found that certain enzyme-inhibitor complexes, in particular Aqualysin I-soybean trypsin inhibitor complexes, were inactive at ambient temperature, and dissociated at elevated temperatures, thereby releasing the enzymes, which enzymes regained their activity.

The present invention is directed to a method for selectively activating a thermostable hydrolase at a temperature above T1, said method comprising the following steps:

a) providing, at a temperature below T1, a composition comprising the thermostable hydrolase and a temperature sensitive inhibitor, wherein said thermostable hydrolase and said temperature sensitive inhibitor form a hydrolase-inhibitor complex at a temperature below T1, wherein said inhibitor inhibits the activity of said hydrolase in said complex at a temperature below T1 and dissociates from said complex at a temperature of about T1, and;

b) elevating the temperature of said composition to a temperature above T1, thereby activating the hydrolase.

In some embodiments, the hydrolase is a protease, preferably a serine protease.

In some embodiments, the hydrolase is Aqualysin I from *Thermus aquaticus* LMG 8924.

In some embodiments, the inhibitor is of vegetable origin or a recombinant, semi-synthetic, or synthetic variant thereof.

In some embodiments, the inhibitor is a trypsin inhibitor, preferably soybean trypsin inhibitor.

In some embodiments, said temperature T1 is at least 40° C., preferably at least 50° C., more preferably at least 60° C.

In some embodiments, said inhibitor is irreversibly inactivated at a temperature of about T1.

In some embodiments, said hydrolase has maximal activity at a temperature above T1.

In some embodiments, the activity of the enzyme in the complex is less than 25% of the activity of the uninhibited enzyme.

The present invention also provides a composition comprising a thermostable hydrolase and a temperature sensitive inhibitor, wherein said thermostable hydrolase and said temperature sensitive inhibitor form a hydrolase-inhibitor complex at a temperature below T1, wherein said inhibitor inhibits the activity of said hydrolase in said complex at a temperature below T1 and dissociates from said complex at a temperature of about T1.

In some embodiments, the hydrolase is a protease, preferably a serine protease, more preferably Aqualysin I from *Thermus aquaticus* LMG 8924.

In some embodiments, the inhibitor is of vegetable origin or a recombinant, semi-synthetic, or synthetic variant thereof.

In some embodiments, the inhibitor is a trypsin inhibitor, preferably soybean trypsin inhibitor.

In some embodiments, said temperature T1 is at least 40° C., preferably at least 50° C., more preferably at least 60° C.

In some embodiments, said inhibitor is irreversibly inactivated at a temperature of about T1.

In some embodiments, said hydrolase has maximal activity at a temperature above T1.

In some embodiments, the activity of the enzyme in the complex is less than 25% of the activity of the uninhibited enzyme.

In some embodiments, the composition is a food or feed composition, or a detergent composition.

In some embodiments, said food or feed composition is a food or feed additive.

In some embodiments, said food additive is a bread or pastry improver.

The invention also relates to the use of the composition as taught herein in the food or feed industry, or in the detergent industry, preferably in the food industry, more preferably for bakery or pastry applications.

In some embodiments, the composition as taught herein is used for improving the crispiness of baked products.

The present invention is further directed to a method for preparing a composition as taught herein, comprising the following steps:
a) mixing the thermostable hydrolase and the temperature sensitive inhibitor in a suitable solvent;
b) allowing the inhibitor to form a complex with the hydrolase by incubating the mixture obtained in step a) at a temperature between 0° C. and 40° C.; and
c) optionally drying, refrigerating, freezing and/or stabilizing the mixture.

These and further aspects and embodiments are described in the following sections and in the claims.

DETAILED DESCRIPTION OF THE INVENTION

Figure 1:
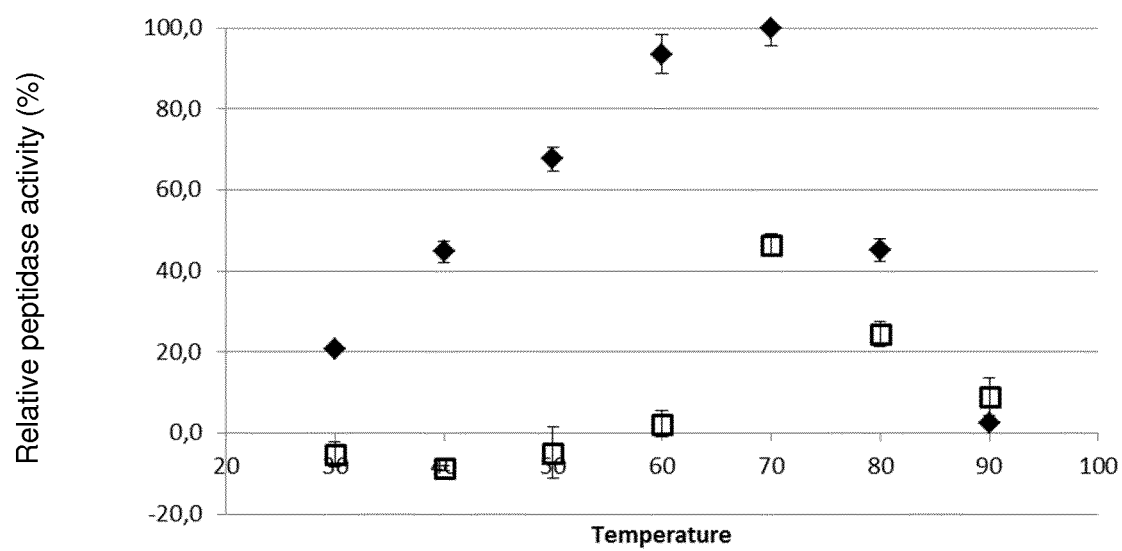
FIG. 1 shows relative activity of Aqualysin I in absence (black diamonds) and presence (open squares) of soybean trypsin inhibitor (SBTI) (Kunitz-type inhibitor) as a function of temperature. The enzymatic activity was colorimetrically determined using the synthetic substrate N-succinyl-Ala-Ala-Pro-Phe-p-nitroanilide (AAPF) and expressed as a percentage of the maximal Aqualysin I activity as measured at 70° C.

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides a method for selectively activating a thermostable hydrolase at a temperature above T1, said method comprising the following steps:
a) providing, at a temperature below T1, a composition comprising the thermostable hydrolase and a temperature sensitive inhibitor, wherein said thermostable hydrolase and said temperature sensitive inhibitor form a hydrolase-inhibitor complex at a temperature below T1, wherein said inhibitor inhibits the activity of said hydrolase in said complex at a temperature below T1 and dissociates from said complex at a temperature of about T1, and;
b) elevating the temperature of said composition to a temperature above T1, thereby activating the hydrolase.

The terms "activate" or "activated" or derivatives thereof are used in their broadest sense herein, and particularly denote increasing or stimulating, to any extent, or providing a property, function, variable, etc. of that what is said to be activated. Where activation effects a determinable or measurable variable, then activation may encompass an increase in the value of said variable by at least about 10°/0, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said activation.

As intended herein, the phrase "activating a hydrolase" particularly denotes increasing or stimulating the activity of a hydrolase beyond the activity of the hydrolase without said activation such as e.g. inhibited hydrolase, or providing hydrolase activity (i.e. rendering an inactive hydrolase functional). In embodiments, said activation comprises rendering an inactive hydrolase active or functional.

In embodiments, the activated hydrolase has an activity of at least 40%, preferably at least 50% or at least 60%, more preferably at least 70% or at least 80%, even more preferably at least 90% or at least 95% of the uninhibited hydrolase (i.e. hydrolase in the absence of inhibitor) as measured at a temperature above T1.

The terms "inhibit" or "inhibited" or derivatives thereof are used in their broadest sense herein, and particularly denote decreasing or reducing, to any extent, abolishing or preventing a property, function, variable, etc. of that what is said to be inhibited. Where inhibition effects a determinable or measurable variable, then inhibition may encompass a decrease or reduction in the value of said variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said inhibition.

As intended herein, the phrase "inhibiting a hydrolase" particularly denotes inhibiting, such as reducing, abolishing or preventing, the activity of a hydrolase below the activity of the uninhibited hydrolase. With "residual activity" is meant herein the activity of the hydrolase in the presence of inhibitor relative to the activity of the hydrolase in the absence of inhibitor. In embodiments, the activity of the hydrolase in the hydrolase-inhibitor complex (i.e. the inhibited hydrolase) as described herein is lower than 25%, preferably lower than 20% or lower than 15%, more preferably lower than 10%, even more preferably lower than 5% of the activity of the uninhibited hydrolase (i.e. the hydrolase in the absence of the inhibitor) as measured at a temperature below T1, such as at room temperature (e.g. at 20.0±2.0° C.). Accordingly, in embodiments the relative activity of the inhibited hydrolase is lower than 25%, preferably lower than 20% or lower than 15%, more preferably lower than 10%, even more preferably lower than 5%, as measured at a temperature below T1, such as at room temperature Enzyme activity can be determined or measured with assays known in the art. Typically, the enzyme is pre-incubated with or without enzyme inhibitor, and the (residual) enzyme activity is then measured upon contacting the enzyme with an appropriate substrate. For example, protease activity can be determined using the synthetic substrate N-succinyl-Ala-Ala-Pro-Phe-p-nitroanalide (AAPF) by colorimetrically measuring the amount of enzymatically formed p-nitroanalide.

The terms "inhibitor" or "enzyme inhibitor" generally refer to a molecule which is able to inhibit the activity of an enzyme. The inhibitor may bind to the enzyme to inhibit it. In "irreversible inhibition", the inhibitor is covalently linked to the enzyme or bound so tightly that its dissociation from the enzyme is very slow. "Reversible inhibition" is characterized by a non-covalent binding of the inhibitor to the enzyme and may be characterized by a rapid equilibrium between the enzyme and the inhibitor. A "competitive inhibitor" blocks the active site of the enzyme and in this way prevents the substrate/active site interaction, thereby diminishing the reaction rate. In the case of competitive inhibition, the inhibitor may mimic the normal substrate of said enzyme. For this type of inhibition, the Dixon plots (inverse of reaction rate, 1/V, versus inhibitor concentration, [I]) corresponding to the different substrate concentrations and the Lineweaver-Burk plots (inverse of reaction rate, 1/V, versus inverse of substrate concentration, 1/[S]) corresponding to different inhibitor concentrations intersect in the left quadrant and the vertical axis, respectively. For "non-competitive inhibition", both inhibitor and substrate can bind to the enzyme and this independent of the binding order. The inhibition may be due to a conformational change of the enzyme at or near the active site, thereby decreasing turn-over number. In the case of non-competitive inhibition, the Dixon and Lineweaver-Burk plots intersect on the horizontal axis in the left quadrant.

The hydrolase inhibitor in the complexes as taught herein may be any type of inhibitor that reversibly inhibits the hydrolase. More particularly, the inhibitor as taught herein inhibits the hydrolase through the formation of a reversible hydrolase-inhibitor complex. The inhibitor may be e.g. a competitive inhibitor or a non-competitive inhibitor.

Inhibitors as used herein are preferably proteins or peptides, more preferably proteins. The term "protein" as used herein generally refers to a macromolecule comprising one or more polypeptide chains, i.e., polymeric chains of amino acid residues linked by peptide bonds. The term may encompass natural, recombinant, semi-synthetical or synthetical produced proteins. The term also encompasses proteins that carry one or more co- or post-expression modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

Inhibitors as used herein may be of biological nature (e.g. isolated from a biological species such as a plant or a micro-organism), recombinant, or (semi-)synthetic. In embodiments, the inhibitor is of vegetable origin (i.e. naturally occurring in plants) or a recombinant or (semi-)synthetic variant thereof. Non-limiting examples of vegetable sources include wheat (*Triticum aestivum*), corn, oats, rye, rice, soybean (*Glycine max*), etc. In embodiments, the vegetable source is selected from the group comprising or consisting of wheat (*Triticum aestivum*), corn, oat, rye, rice, and soybean (*Glycine max*). In particular embodiments, the inhibitor originates from soybean or is a recombinant or (semi-)synthetic variant thereof.

The term "enzyme" generally refers to a molecule catalyzing a chemical reaction. The enzymes used herein are preferably hydrolases. With "hydrolase" is meant herein an enzyme that catalyzes the hydrolysis (i.e. the cleavage of chemical bonds by the addition of water) of a chemical bond. Non-limiting examples of hydrolases include the enzymes as classified as E.C. 3, such as proteases (or peptidases), dehalogenases, deacetylases, nitrilases, lactamases, glucosidases, phosphatases, diphosphatases, amylases, lipases, beta glucanases, cellulases, lipases, oxidases, lipoxygenases, dehydrogenases, laccases, etc.

In embodiments, the hydrolase is selected from the group comprising cellulolytic and/or glucanolytic enzymes (also referred to as cellulases (EC:3.2.1.4), amylases (EC:3.2.1.1) and/or hemicellulases), 1,3-xylosidases (such as EC: 3.2.1.72), alpha-L-arabinofuranosidases (such as EC: 3.2.1.55), 1,3-1,4-glucanases (such as EC:3.2.1.73 or such as 3.2.1.6) and hydrolases of peptide bonds (also referred to as proteases or peptidases (EC: 3.4), such as serine peptidases (EC: 3.4.21)).

In preferred embodiments, the hydrolase is a protease. The terms "protease", "peptidase" and "peptide hydrolase" are used as synonyms herein and denote hydrolases which catalyze the hydrolysis of peptide bonds. In particular embodiments, the hydrolase is a serine protease, more particularly Aqualysin I from *Thermus aquaticus*, more particularly *Thermus aquaticus* LMG 8924.

In particular embodiments, the hydrolase is a protease, preferably a serine protease, and the inhibitor is a trypsin inhibitor. For example, the hydrolase may be Aqualysin I from *Thermus aquaticus*, more particularly *Thermus aquaticus* LMG 8924, and the inhibitor may be soybean trypsin inhibitor.

In embodiments, the hydrolase may be Aqualysin I from *Thermus aquaticus*, more particularly *Thermus aquaticus* LMG 8924, and the inhibitor may be a wheat extract, a rice extract, an oat extract, or a rye extract.

The expression "temperature sensitive" as used herein in connection with the inhibitor denotes that the stability of the inhibitor is temperature dependent. A temperature sensitive inhibitor as used herein particularly denotes an inhibitor which becomes irreversibly inactivated at elevated temperatures, more particularly at a temperature of about T1 or higher. In embodiments, the temperature sensitive inhibitor is irreversibly inactivated at a temperature of about T1. A non-limiting example of a temperature sensitive inhibitor is soybean trypsin inhibitor (SBTI).

The term "thermostable" as used herein in connection with the enzyme, in particular the hydrolase, means that the enzyme, in particular the hydrolase, is resistant to irreversible inactivation (e.g. due to irreversible changes in its chemical structure such as denaturation) at elevated temperatures, more particularly at a temperature above T1. Hence, the temperature T1 is preferably below the denaturation temperature of the hydrolase. A non-limiting example of a thermostable hydrolase is Aqualysin I.

Preferably, the hydrolase as taught herein is a "thermophilic" hydrolase, i.e. a hydrolase which is active at elevated temperatures, in particular at temperatures above T1. An advantage of using thermophilic hydrolases is that the chemical reaction rate increases with increasing the temperature of the industrial process. In embodiments, the hydrolase as taught herein has a maximal activity at 40° C. or higher, preferably at 50° C. or higher, more preferably at 60° C. or higher, even more preferably at 70° C. or higher.

"T1" as used herein denotes the temperature at which the hydrolase-inhibitor complex as taught herein dissociates. Said temperature T1 is preferably at least 40° C., such as at least 45° C., more preferably at least 50° C., such as at least 52° C., at least 54° C., at least 55° C., at least 56° C., or at least 58° C., even more preferably at least 60° C.

The term "dissociation" as used herein denotes the process wherein the hydrolase-inhibitor complex as taught herein falls apart or breaks down, thereby releasing the hydrolase and the inhibitor. In embodiments, the dissociation of the hydrolase-inhibitor complex is reversible. In case the dissociation is reversible, the hydrolase-inhibitor complex may re-associate upon decreasing the temperature below T1. In other embodiments, the dissociation of the hydrolase-inhibitor complex is irreversible, e.g. in case the inhibitor becomes irreversibly inactivated at a temperature of about T1.

The invention also relates to a composition comprising a thermostable hydrolase and a temperature sensitive inhibitor, wherein said thermostable hydrolase and said temperature sensitive inhibitor form a hydrolase-inhibitor complex at a temperature below T1, wherein said inhibitor inhibits the activity of said hydrolase in said complex at a temperature below T1 and dissociates from said complex at a temperature of about T1.

The compositions as taught herein may comprise one or more, such as two, three, four, etc. hydrolase-inhibitor complexes.

In addition to the thermostable hydrolase and the temperature sensitive inhibitor as taught herein, the composition as taught herein may further comprise one or more suitable carriers or excipients. Non-limiting examples of "carriers" or "excipients" includes any and all of solvents, diluents, buffers, solubilisers, colloids, dispersion media, vehicles, fillers, cereal flours, fiber (such as e.g. oat fiber), proteins, lipids (such as e.g. margarine, butter, oil, and shortenings), salts, starches, sugars, polysaccharides, polyols, alkalis (such as e.g. sodium carbonate, sodium bicarbonate, sodium silicate, sodium citrate and ammonium hydroxide), antioxidants (such as e.g. ascorbic acid, glutathione, cysteine), emulsifiers (such as e.g. diacetyl tartaric acid esters of monoglycerides (DATEM), sodium stearoyl lactylate (SSL), calcium stearoyl lactylate (CSL), glycerol monostearate (GMS), rhamnolipids, lecithins, sucroesters and bile salts), vitamins (such as e.g. pantothenic acid and vitamin E), sweeteners, colorants, flavourings, aromatisers, thickening agents (such as e.g. gums), surfactants (such as e.g. linear alkyl sulphonates (LAS), alkyl aryl sulphonates such as dodecylbenzene sulfonate (DDBS), alcohol ether sulphates such as sodium lauryl ether sulfate (SLES), alcohol ethoxylates, and long-chain quaternary ammonium compounds), builders (such as e.g. sodium tripolyphosphate (STPP), citrates, tartrates, succinates, gluconates, polycarboxylates, ethylenediamine tetraacetic acid (EDTA), diethylene triamine pentaacetic acid (DTPA), hydroxyethylene diamine triacetic acid (HEDTA), dihydroxyethyl glycine (DEG), and triethanolamine), anti-redeposition agents (such as e.g. carboxy methyl cellulose (CMC), polyvinyl pyrrolidone, polyethylene glycol (PEG) and polyvinyl alcohol), active oxygen bleaches (such as e.g. sodium percarbonate), antimicrobial agents (such as e.g. quaternary ammonium chlorides and alcohols), antifungal agents, fabric softeners (such as e.g. long-chain amines and long-chain quaternary ammonium compounds), one or more fragrances, one or more optical brighteners (such as e.g. aminotriazines, coumarins, and stilbenes), one or more preservatives (such as e.g. glutaraldehyde and EDTA), hydrotopes (such as e.g. xylenesulfonate, cumenesulfonate, some glycol ether sulphates, and urea), foam regulators (such as soaps, siloxanes and paraffins), corrosion inhibitors (such as e.g. sodium silicate), chelating agents (such as, e.g., EDTA or glutathione), disintegrants, binders, lubricants, wetting agents, and the like.

Compositions as taught herein may advantageously be employed in various applications, more particularly in applications which require an active hydrolase at elevated temperatures, but wherein the activity of said hydrolase at lower temperatures, in particular at ambient temperature, is preferably inhibited. Non-limiting examples include the use of the compositions as taught herein in the food industry, e.g. for baking, for pastry applications, brewing (for clarification of beer), preparation of digestive aids, production of fruit juices (for clarification of fruit juices) and starch syrups, production of spirits and in the alcohol industry; in the feed industry, e.g. for feed pellets and pet food production; in textile industry, e.g. for desizing, for biobleaching of wood or silk; in paper industry, e.g. for bleaching of paper, for processing of cellulose; for the production of biofuel; in the detergent industry, e.g. as additive in laundry or dish detergents or surface cleaning; for starch conversion; in the pharmaceutical industry, e.g. for the production of pharmaceutical components such as chitosan, etc.

In embodiments, the compositions as taught herein are food or feed additives, such as e.g. bread or pastry improvers, or detergent compositions, such as e.g. laundry detergents and dish detergents.

"Bread improvers" (also referred to as "dough improvers" or "improving agent" or "flour treatment agent") are typically added to the dough during baking in order to improve texture, volume, flavour and freshness of the baked product as well as to improve machinability and stability of the dough. Typically, a bread improver comprises or consists of: one or more enzymes (such as e.g. amylases, xylanases, lipases, oxidases, lipoxygenases, proteases, dehydrogenases and laccases), one or more oxidizing or reducing agents (such as e.g. ascorbic acid, glutathione, cysteine), one or more emulsifiers (such as e.g. diacetyl tartaric acid esters of monoglycerides (DATEM), sodium stearoyl lactylate (SSL), calcium stearoyl lactylate (CSL), glycerol monostearate (GMS), rhamnolipids, lecithins, sucroesters, bile salts), one or more lipid materials (such as e.g. margarine, butter, oil, shortening), one or more vitamins (such as e.g. pantothenic acid and vitamin E), one or more gums, and/or one or more sources of fibre (such as e.g. oat fibre).

In animal feed, enzymes have been used as feed additives for decades. Some enzymes have been shown to improve one or both of the animal absolute body weight gain (BWG) and the Feed Conversion Ratio (FCR) of a given feed. Enzymes used in feed may for example allow nutritionists to reduce the energy and/or protein requirements in the diets without affecting the zootechnical performances of animals. Animal feed, including silage, pelletized feed and mash feed, comprises mainly feedstuffs and feed additives among which enzymes. Feedstuffs may be plant materials such as cereals, legumes, beet molasse, potato pulps, peanut meal and biofuel products or being animal products such as fish meal, meat and bone meal, insect meal, etc.

Detergent compositions typically comprise or consist of: one or more surfactants (such as e.g. linear alkyl sulphonates (LAS), alkyl aryl sulphonates such as dodecylbenzene sulfonate (DDBS), and alcohol ether sulphates such as sodium lauryl ether sulfate (SLES), alcohol ethoxylates, and long-chain quaternary ammonium compounds), one or more builders (such as e.g. sodium tripolyphosphate (STPP), citrates, tartrates, succinates, gluconates, polycarboxylates, ethylenediamine tetraacetic acid (EDTA), diethylene triamine pentaacetic acid (DTPA), hydroxyethylene diamine triacetic acid (HEDTA), dihydroxyethyl glycine (DEG), and triethanolamine), one or more alkalis (such as e.g. sodium carbonate, sodium bicarbonate, sodium silicate, sodium citrate and ammonium hydroxide), anti-redeposition agents (such as e.g. carboxy methyl cellulose (CMC), Polyvinyl pyrrolidone, polyethylene glycol (PEG) and polyvinyl alcohol), one or more enzymes (such as e.g. peptidase, amylases and lipases), one or more active oxygen bleaches (such as e.g. sodium percarbonate), one or more antimicrobial agents (such as e.g. quaternary ammonium chlorides and alcohols), one or more fabric softeners (such as e.g. long-chain amines and long-chain quaternary ammonium compounds), one or more fragrances, one or more optical brighteners (such as e.g. aminotriazines, coumarins, and stilbenes), one or more preservatives (such as e.g. glutaraldehyde and EDTA), one or more hydrotopes (such as e.g. xylenesulfonate, cumenesulfonate, some glycol ether sulphates, and urea), one or more foam regulators (such as soaps, siloxanes and paraffins), and/or one or more corrosion inhibitors (such as e.g. sodium silicate).

Also described herein is the use of the hydrolase-inhibitor complexes or the compositions as taught herein in the food or feed industry, in the detergent industry, in the paper industry, in the textile industry, for the production of biofuel, and/or in the pharmaceutical industry.

An embodiment relates to the use of the hydrolase-inhibitor complexes or the compositions as taught herein in the feed industry.

An embodiment relates to the use of the hydrolase-inhibitor complexes or the compositions as taught herein in the detergent industry.

An embodiment relates to the use of the hydrolase-inhibitor complexes or the compositions as taught herein in the food industry. A further embodiment relates to the use of the hydrolase-inhibitor complexes or the compositions as taught herein in bakery or pastry applications.

A particular embodiment relates to the use of the hydrolase-inhibitor complexes or the compositions as taught herein for improving the crispiness of baked products, in particular bread products, more particularly to retain the crispy crust of baked products, in particular bread products, for a considerable time after baking. Also disclosed herein is a method for improving the crispiness of baked products, in particular bread products, more particularly for retaining the crispy crust of baked products, in particular bread products, for a considerable time after baking, said method comprising applying a composition as taught herein onto the outside of a dough or a partly baked product, in particularly bread product.

"Bread products" include soft bread products and crusty products. "Soft bread products" present a soft crust, including amongst others all packed bakery goods and sweet goods (packed or unpacked). Non-limiting examples of soft bread products are bread, soft rolls, donuts, buns, microwavable buns, Danish pastry, hamburger rolls, pizza and pita bread. "Crusty products" have a crusty crust. They are usually unpacked or wrapped with paper packaging. Non-limiting examples of crusty products are baguettes and rolls.

"Cakes" are batter-based baked products prepared with three major ingredients present in different ratios depending on the type of cake: flour, sugar and eggs (whole eggs and/or egg white and/or egg yolk). Additional ingredients may be for example fats and/or lipids, leavening agents, emulsifiers, milk proteins, hydrocolloids, starch (native, chemically or physically modified), cocoa powder, chocolate, coloring agents, flavors, etc. Cakes may be leavened due to addition of ingredients (e.g. baking powder, egg, emulsifier, protein . . . ) and/or due to the cake preparation process (e.g. whipping of the batter). Typical types of cakes are loaf cream and pound cakes, cup cream and pound cakes, sponge cakes, muffins, cake donuts, brownies, etc.

Another aspect of the present invention relates to a method for preparing the compositions as taught herein, said method comprising the following steps:
  a) mixing the thermostable hydrolase and the temperature sensitive inhibitor in a suitable solvent;

b) allowing the inhibitor to form a complex with the hydrolase by incubating the mixture obtained in step a) at a temperature below T1; and c) optionally drying, refrigerating, freezing and/or stabilizing the mixture.

The hydrolase and the inhibitor may be provided in liquid state or as a solid.

The solvent is preferably a liquid. A "suitable solvent" denotes a solvent which is compatible with the other components of the composition, more particularly which is compatible with the hydrolase (i.e. which does not affect the stability of the hydrolase). Non-limiting examples of suitable solvents include buffers such as e.g. sodium acetate buffer or sodium borate buffer.

The mixture obtained in step a) may be e.g. a solution or a suspension.

The incubation of the mixture of the temperature sensitive inhibitor and the thermostable hydrolase obtained in step a) must be conducted at a temperature below T1 to allow the hydrolase-inhibitor complex to form. In embodiments, the incubation is conducted at a temperature of at least 10° C. below T1, preferably at least 15° C. below T1, more preferably at least 20° C. below T1, such as at least 25° C., 30° C., 35° C. or 40° C. below T1. Preferably, the incubation is conducted at a temperature between 0° C. and about 40° C., preferably between about 10° C. and about 30° C., more preferably between about 15° C. and about 25° C., such as at about 20° C.

The incubation is performed for a time sufficient to achieve inhibition of the hydrolase activity. Preferably, the enzyme activity is inhibited by at least 75%, preferably by at least 80% or at least 85%, more preferably by at least 90%, even more preferably by at least 95%, and most preferably by 100% (i.e. inactive enzyme) relative to the enzyme activity of uninhibited enzyme (i.e. enzyme in the absence of inhibitor) as measured at ambient temperature (i.e. at a temperature between about 10° C. and about 30° C., preferably between about 15° C. and about 25° C., such as about 20° C.). Typically, the incubation time may range from about 5 minutes to about 2 hours, preferably from about 10 minutes to about 1 hour, such as about 30 minutes.

The mixture obtained in step b) following incubation may be used as such, or can be further processed. For example, the mixture may be dried, cooled or refrigerated, frozen, and/or stabilized. Accordingly, in embodiments, the method as taught herein may further comprise a step c), wherein one or more of the following processing steps may be performed: drying of the mixture, cooling of the mixture, freezing of the mixture, and stabilizing the mixture.

Drying of the mixture may be achieved e.g. by spray drying, freeze-drying, fluid-bed drying, drum drying, film drying, flash drying, ring drying, infra-red drying, extrusion, or agglomeration.

The mixture may be cooled at a temperature below 10° C., preferably below 8° C., more preferably below 5° C. (i.e. refrigeration).

The mixture may be frozen at a temperature below 0° C., preferably below −10° C., more preferably below −20° C.

To stabilize the mixture, suitable stabilizers such as e.g. glycerol, salt(s) and preservatives, may be added.

As described above, the composition as taught herein may further comprise one or more carriers or excipients. These can be added to the mixture before or after the further processing steps.

The present invention will further be described in the following examples without limiting the scope of the present invention.

EXAMPLES

Example 1

Peptidase-Peptidase Inhibitor Complexes

Methods

Peptidase Activity Assay

Peptidase activity was colorimetrically determined using the synthetic substrate N-succinyl-Ala-Ala-Pro-Phe-p-nitroanilide (AAPF). The peptidase was Aqualysin I (Aq I), an endo-working thermophilic alkaline serine peptidase produced by *Thermus aquaticus* LMG 8924. The assay mixture comprised 45 μL of an appropriately diluted enzyme solution [0.95 μM of Aq I] mixed with 60 μL 50 mM sodium borate buffer (pH 10.0) and 60 μL substrate solution [1.28 mM AAPF in 50 mM sodium borate buffer (pH 10.0)], and was heated for exactly 20 min at different incubation temperatures (30° C., 40° C., 50° C., 60° C., 70° C., 80° C. and 90° C.). Immediately after heating, all samples were cooled in ice-cold water, 100 μl of the reaction volume was transferred to a microtiter plate and the absorbance at 415 nm (Abs 415 nm) was determined at room temperature to measure the amount of enzymatically formed p-nitroanilide. Each sample was analyzed in triplicate.

Peptidase Activity in the Presence of Peptidase Inhibitor

The inhibitor was soybean trypsin inhibitor (SBTI) from *Glycine max* (soybean) (Sigma-Aldrich, Bornem, Belgium). A mixture (45 μl) containing 0.95 μM of Aq I and 95.7 μM of SBTI was prepared and pre-incubated for 30 min at room temperature. This mixture was used in the assay mixture as described above instead of the enzyme solution. Samples were incubated for exactly 20 min at different incubation temperatures (40° C., 50° C., 60° C., 70° C., 75° C., 80° C. and 90° C.). Immediately after heating, all samples were cooled in ice-cold water, 100 μl of the reaction volume was transferred to a microtiter plate and the extinction at 415 nm was measured against a control, prepared by incubating the assay mixture with water instead of enzyme solution. All samples were analyzed in triplicate.

Results

At lower incubation temperatures the impact of inhibitor was more pronounced than at higher temperatures (FIG. 1). In the presence of sufficient inhibitor, no Aq I activity was measured during incubation at temperatures up to 60° C. In contrast, at 70° C. and at 80° C. the relative (compared to Aq I activity in the absence of inhibitor) Aq I activity in the presence of the same amount of inhibitor remained about 50%.

These results show that during pre-incubation Aq I interacts with SBTI to form an enzyme-inhibitor complex with a temperature-dependent stability. At 60° C., the relative activity of Aq I is not significantly different from that at lower temperatures (30-50° C.). This indicates that up to 60° C. the enzyme-inhibitor complex is relatively stable. At higher temperatures (from 60 to 80° C.), the impact of inhibitor decreases due to a temperature-dependent dissociation of the enzyme-inhibitor complex.

In the absence of inhibitor, Aq I activity is highest at 70° C. At temperatures exceeding 70° C., Aq I activity decreases due to enzyme denaturation as described by Matsuzawa et al. (1988, European Journal of Biochemisty: 171, 441-447).

Under the present experimental conditions, no Aq I activity was measured in the presence of inhibitor at incubation temperatures up to 60° C. Incubation of Aq I in the presence of inhibitor at 70° C. and 80° C. resulted in residual Aq I activities of approximately 50% of the Aq I activity in the absence of inhibitor. At temperatures higher than 80° C., the presence of inhibitor had no impact on the Aq I activity.

Example 2

Use of Peptidase-peptidase Inhibitor Complexes for Improving the Crispiness of Bread Products Methods Enzyme-inhibitor complexes comprising Aq I and soybean trypsin inhibitor (Sigma-Aldrich, Bornem, Belgium) were applied on the surface of frozen stored bread roll dough samples. Frozen stored bread roll dough was bought from a local super market (AVEVE Group, Leuven, Belgium).

Prior to thawing and fermentation, the frozen roll dough samples were consecutively soaked in liquid nitrogen (to uniformly freeze the surface of all bread roll dough samples before soaking) and in an aqueous solution with 1) enzyme-inhibitor complexes, 2) enzyme alone (at a concentration of 8.54 nmol/mL tap water), 3) inhibitor alone (at a concentration of 853.73 nmol/mL tap water, or 4) in tap water without additives (control). The solution with enzyme-inhibitor complexes contained 8.54 nmol/mL tap water enzyme and 853.73 nmol/mL tap water inhibitor to obtain 100% enzyme inhibition, and was equilibrated for 30 min to ensure the formation of enzyme-inhibitor complexes. By soaking the frozen bread roll dough samples in the aqueous solution, it was ensured that the enzyme, whether or not after being released from the inhibitor, only modified the surface of the dough/bread roll during baking.

Bread roll dough mass was determined before and after soaking in the aqueous solutions or the tap water.

The soaked bread roll dough samples were then fermented (at 33° C. and 95% relative humidity) for 4 h in a fermentation cabinet (National Manufacturing, Lincoln, Neb., USA). Baking was performed in a Condilux deck oven (Hein, Strasse, Luxemburg) for 20 min at 220° C. top and bottom heat.

Water activity of the crust, which is a measure for crust crispness (Primo-Martinet et al. 2006 Journal of Cereal Science 43(3): 342-352), was determined after 1, 2 and 4 hours of cooling.

Results

Figure 2:
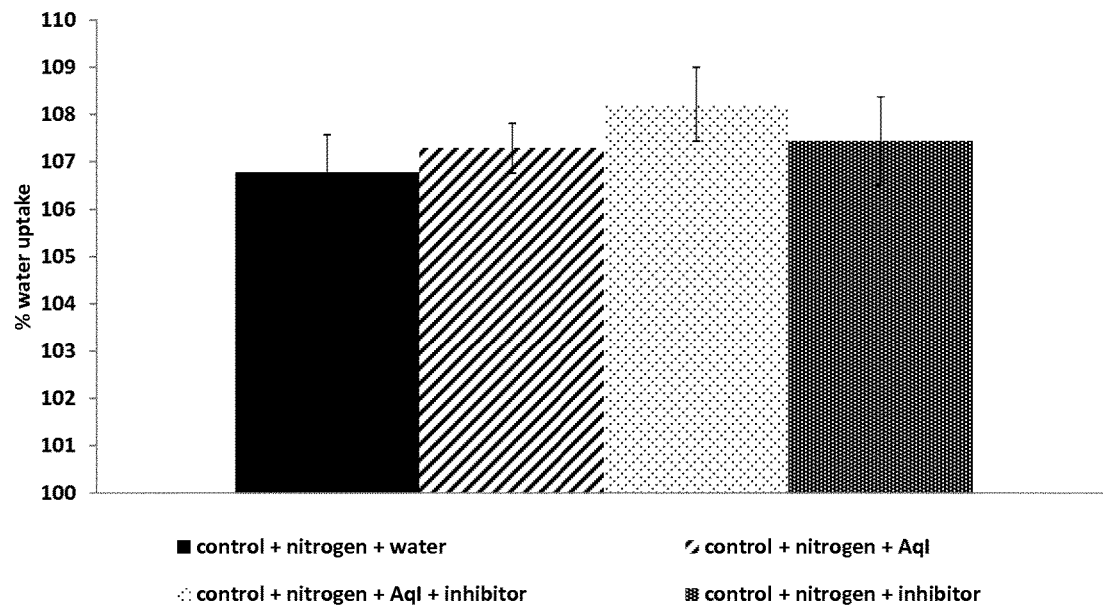
FIG. 2 shows the percentage water uptake during soaking of bread roll doughs as determined by measuring the dough mass before and after soaking. The different soaking solutions were tap water, tap water with Aqualysin I (AqI), tap water with soybean trypsin inhibitor (SBTI), and tap water with AqI-SBTI complexes.

For all experiments, a similar amount of water could be added to the dough surfaces as evidenced by FIG. 2 which shows the increase in dough mass before and after soaking.

Figure 3:
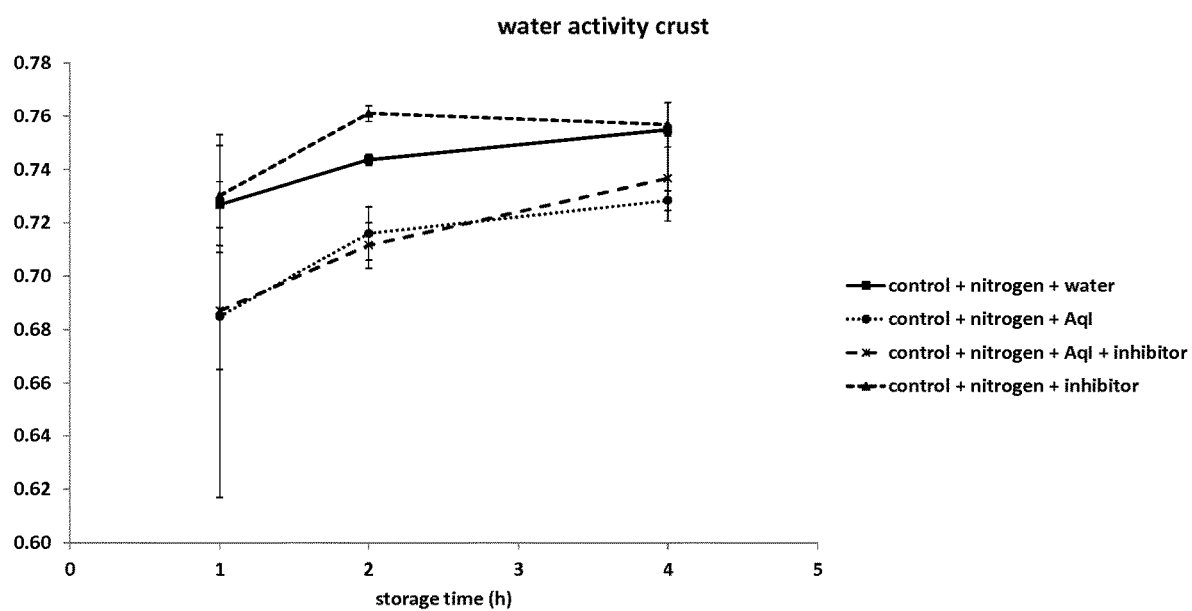
FIG. 3 shows water activity of the crust of bread rolls as measured after 1, 2 or 4 hours of cooling. Prior to fermentation and baking, the dough for the bread rolls was soaked in either tap water, tap water with Aqualysin I (AqI), tap water with soybean trypsin inhibitor (SBTI), or tap water with AqI-SBTI complexes.

FIG. 3 shows, especially after 2 h of cooling, that bread rolls from dough samples previously soaked in enzyme or enzyme-inhibitor complex solutions had a lower water activity and, thus, a more crispy crust compared to bread rolls soaked in water (control) or in water with only inhibitor present. The water activity of bread rolls from dough samples previously soaked in enzyme and enzyme-inhibitor complex solutions was substantially the same, indicating that the enzyme added as a complex with inhibitor was able to perform a hydrolytic activity which resulted in similar crust water activity compared to the enzyme added without inhibitor.

The invention claimed is:

1. Method for selectively activating a thermostable hydrolase at a temperature above T1, said method comprising the following steps:
   a) providing, at a temperature below T1, a composition comprising the thermostable hydrolase and a temperature sensitive inhibitor, wherein the hydrolase is a serine protease, and said inhibitor is of vegetable origin or a recombinant, semi-synthetic or synthetic variant thereof, and wherein said thermostable hydrolase and said temperature sensitive inhibitor form a hydrolase-inhibitor complex at a temperature below T1, wherein said inhibitor inhibits the activity of said hydrolase in said complex at a temperature below T1 and dissociates from said complex at a temperature of about T1, and;
   b) elevating the temperature of said composition to a temperature above T1, thereby activating the hydrolase;
   wherein T1 is the temperature at which the hydrolase-inhibitor complex dissociates and is at least 60° C.

2. Method according to claim 1, wherein the hydrolase is Aqualysin I from *Thermus aquaticus* LMG 8924.

3. Method according to claim 1, wherein the inhibitor is a trypsin inhibitor.

4. Method according to claim 1, wherein said inhibitor is irreversibly inactivated at a temperature of about T1.

5. Method according to claim 1, wherein said hydrolase has maximal activity at a temperature above T1.

6. Method according to claim 1, wherein the activity of the enzyme in the complex is less than 25% of the activity of the uninhibited enzyme.

7. Method according to claim 3, wherein the inhibitor is a soybean trypsin inhibitor.

* * * * *